United States Patent [19]

Sinclair

[11] Patent Number: 4,882,335

[45] Date of Patent: Nov. 21, 1989

[54] METHOD FOR TREATING ALCOHOL-DRINKING RESPONSE

[75] Inventor: John D. Sinclair, Espoo, Finland

[73] Assignee: Alko Limited, Helsinki, Finland

[21] Appl. No.: 205,758

[22] Filed: Jun. 13, 1988

[51] Int. Cl.$^4$ ............................................. A61K 31/44
[52] U.S. Cl. ..................................... 514/282; 514/811
[58] Field of Search ................ 514/810, 811, 812, 282

[56] References Cited

PUBLICATIONS

Chem. Abst., 106-12821P, (1987).
"Naloxone Persistently Modifies Water-Intake", Pharmacology Biochemistry & Behavior, Mar. 25, 1986, vol. 29, pp. 331-334.
"Feasibility of Effective Psychopharmacological Treatments for Alcoholism", J. D. Sinclair, Ph.D, British Journal of Addition, 1987, 82, 1213-1223.

Primary Examiner—Stanley J. Friedman
Attorney, Agent, or Firm—Armstrong, Nikaido, Marmelstein, Kubovcik & Murray

[57] ABSTRACT

A therapeutic method is provided for use as an adjunct in the treatment of alcoholism. The method consists of extinguishing the alcohol-drinking response of alcoholics during a relatively short period of time by having them drink alcoholic beverage repeatedly while an opiate antagonist blocks the positive reinforcement effects of ethanol in the brain.

8 Claims, 3 Drawing Sheets

METHOD FOR TREATING ALCOHOL-DRINKING RESPONSE

FIELD OF THE INVENTION

The invention is a treatment for alcohol abuse in which the alcohol-drinking response is extinguished over a limited number of sessions by being emitted while the reinforcement from alcohol is blocked with an opiate antagonist such as naloxone or naltrexone.

BACKGROUND OF THE INVENTION

Alcoholism is the most costly health problem in many countries. The cost, e.g., in America is estimated to be about $117,000,000,000 per year. The treatment methods currently used are not very effective. Most alcoholics drop out of treatment within a month or two. Few alcoholics, regardless of the type of treatment, are able to avoid relapses and renewed alcohol abuse.

No one is born an alcoholic. The drinking of alcohol (ethanol or ethyl alcohol) is a learned response, reinforced largely by the rewarding effects of alcohol in the central nervous system—the euphoria from lower, stimulatory doses of ethanol. An alcoholic is a person who, through an interplay of genetic and environmental factors, has had the alcohol-drinking response reinforced so often and so well that it becomes too strong for the individual to continue functioning properly in society. The strong alcohol-drinking response—i.e., the drive for alcohol—then dominates the person's behavior and life.

The current methods for treating alcoholism are not very successful probably because they do not effectively weaken the alcoholic's alcohol-drinking response. Some methods (e.g., counselling, Alcoholics Anonymous) are aimed at increasing the alcoholic's ability or will power to withstand the drive for alcohol. The drive, however, is not weakened and the patient is told that he will remain an alcoholic, that is, a person with an overly strong alcohol-drinking response, for the rest of his life. These methods succeed in some alcoholics, but in most the time eventually comes when a momentary decrease in will power causes a resumption of alcohol drinking and alcohol abuse.

Other treatments use punishment of various sorts (e.g., electric shock, disulfiram reactions, loss of a job) to try to stop alcohol drinking. Punishment is, however, a poor method for changing behavior and has many limitations. In particular, it is ineffective when positive reinforcement is still being received for the same response that is punished. Since the treatments that punish alcohol drinking do not block the positive reinforcement of the same response coming from alcohol in the brain, they should not be expected to be very effective.

A third type of treatment has been proposed. Alcohol and opiates appear to cause positive reinforcement largely through the same neuronal system in the brain. Consequently, opiates such as morphine or methadone might be able to satisfy the drive for alcohol and thus abolish alcohol drinking. This does indeed occur in rats and other animals, and there is evidence suggesting opiates could also succeed in making alcoholics stop drinking alcohol. The treatment probably would, however, turn alcoholics into opiate addicts, which is, of course, not a good solution.

Instead of counteracting the drive for alcohol or temporarily satisfying it, a successful treatment for alcoholics should permanently weaken the alcohol-drinking response. Fortunately, there is a well-established method for weakening a learned response: "extinction". Extinction consists of having the response emitted repeatedly in the absence of positive reinforcement.

It is relatively simple to remove external sources of positive reinforcement, such as the food a rat gets for pressing a lever or even the social reinforcement a person sometimes gets for drinking alcohol. But much of the positive reinforcement for alcohol drinking is internal, from the rewarding effects of alcohol in the brain.

The results showing that alcohol and opiates share a common mechanism of reinforcement show how the internal positive reinforcement from alcohol might be blocked. Various substances, called opiate antagonists, are able to block the receptors for opiates and thus prevent the effects of, e.g. morphine. Furthermore, there is already evidence that the two most commonly used opiate antagonists, naloxone and naltrexone, do block positive reinforcement from alcohol. First, they block the stimulatory effect of alcohol which is generally thought to be related to the euphoria and positive reinforcement. Second, it has been shown that while they are in the body they reduce voluntary alcohol drinking and intragastric self-administration of alcohol by animals.

Naloxone and naltrexone were originally intended for use in treating overdoses of opiates. They have since been suggested for use against a wide variety of problems including respiratory failure, anorexia nervosa, bulimia, obesity, emesis and nausea, shock, severe itching, constipation, growth of neoplasms, and sexual impotence and frigidity. There have been many studies attempting to use naloxone to reverse alcohol intoxication and especially the coma produced by very large amounts of alcohol; although the results have been mixed and there is still controversy as to whether naloxone can antagonize severe alcohol intoxication, it is important to note that none of these studies reported any bad effects from giving naloxone in conjunction with alcohol. The doses of naloxone have ranged between about 0.2 and 30 mg daily, and naltrexone from about 20 to 300 mg daily. Other suggested uses are for the opiate antagonists in conjunction with other drugs, particularly, opiate agonists. For instance, U.S. Pat. No. 3,966,940 is for a compound containing narcotics or analgesics plus naloxone to be given especially to narcotic addicts. In these cases the opiate or other drug is seen to be active pharmacological agent and the opiate antagonist is included to counteract some of its effects.

Continual treatment with opiate antagonists should reduce the alcohol intake of alcoholics: so long as the antagonist is in the body, the alcoholic should have little incentive for drinking because alcohol is not rewarding. This maintenance treatment, however, has the same problem found with other long-term deterrent treatments, such as that with disulfiram: how to keep the alcoholic on the medication. Since there is still a strong drive for alcohol, the alcoholic is likely to drop out of treatment and stop taking the antagonist so that he or she can satisfy the drive by drinking again.

However, combining the well-established procedure of extinction from psychology with the pharmacological findings that opiate antagonists block reinforcement from alcohol provides a new and much more promising way of treating alcoholism. Indeed, it provides what could be called the first true cure for alcoholism. After a relatively short period of treatment during which an opiate antagonist is employed in extinction therapy, the patient is no longer an alcoholic, because the overly-strong alcohol-drinking response that made the patient be an alcoholic is extinguished. The method for using this extinction procedure is the present invention.

The idea of using extinction therapy with an opiate antagonists for alcoholics has not been suggested previously. A similar idea with naltrexone has, however, been suggested for opiate addicts (see P. F. Renault, NIDA Research Monograph No. 28, pp. 11–22, 1981), but extinction was not included in the design of the clinical tests. The patients were simply detoxified, given naltrexone or placebo, and released. There was no program for encouraging them to take opiates while under the influence of naltrexone, as required for extinction. Consequently, the general result was what would likely happen also with such a naltrexone maintenance program with alcoholics: a very large percentage of the addicts dropped out, stopped taking naltrexone, and started taking opiates again. Of the total of 1005 subjects, however, "17 of the naltrexone and 18 of the placebo subjects actually tested the blockade by using an opiate agonist" when naltrexone would have been active, and "in this subsample, the naltrexone patients had significantly fewer subsequent urines positive for methadone or morphine . . . The pattern in the naltrexone group was to test once or twice with heroin or methadone and then to stop. The use of these drugs in the placebo group was sporadic during the entire course of treatment . . . [Also, on an analog craving scale] the naltrexone patients reported significantly less craving toward the end of their evaluation than did the placebo-treated patients."

These results suggest that naltrexone would be much more useful against opiate addiction if the addicts were given extinction sessions in which they were encouraged to use narcotics while the positive reinforcement was blocked. Furthermore, in relation to the present invention, by showing the extinction therapy with naltrexone does work in humans, they support the hypothesis that it would reduce alcohol abuse and the craving for alcohol in alcoholics.

The example included here shows that the extinction procedure progressively decreases and eventually almost abolishes alcohol drinking by rats and that alcohol intake remains reduced long after all naloxone should have been removed from the body. The high predictive validity of this animal model for indicating treatments that affect human alcohol consumption is discussed in Sinclair, *British Journal of Addiction* 82, 1213–1223 (1987).

SUMMARY OF THE INVENTION

The present invention contemplates a therapeutic method, utilizing the ability of opiate antagonists to block the positive reinforcement from alcohol, to extinguish the alcohol-drinking response of alcoholics. The extinction program consists of numerous sessions in which the alcoholic has an opiate antagonist administered and then drinks alcohol.

The extinction procedure abolishes the alcoholic's strong alcohol-drinking response. Optimally, the patient's drive for alcohol is returned to the level present before he or she ever tasted alcohol. Thus, by definition, the patient is no longer an alcoholic.

Admittedly, the patient can relearn the alcohol-drinking response and become an alcoholic again, and relearning a response that has been extinguished occurs more rapidly than the initial acquisition. But with the first-hand knowledge of the consequences of the first acquisition of alcoholism, and with even a moderate level of will power and outside support, most alcoholics will avoid making the same mistake twice.

This extinction procedure is a useful adjunct for various other methods of treating alcoholics, including punishment of alcohol drinking, procedures to improve will power and social rehabilitation, and maintenance procedures for preventing renewed use of alcohol. These other methods have previously been very limited because of the continuing high drive for alcohol, but they should be much more effective once the alcohol-drinking response has been extinguished.

DESCRIPTION OF THE PREFERRED EMBODIMENTS

Figure 1:
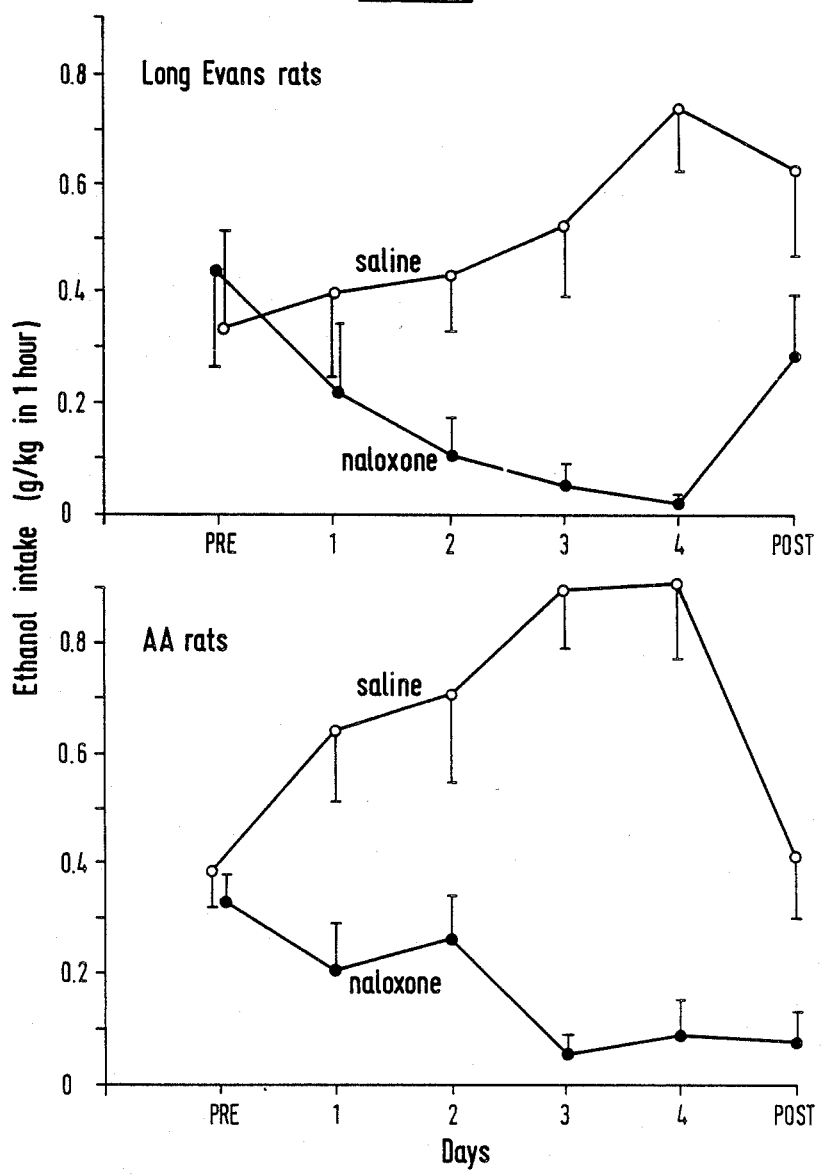
FIG. 1 shows the apparent extinction of alcohol drinking in Long Evans and AA rats caused by 4 daily sessions of drinking alcohol after administration of naloxone (mean±standard error).

The extinction procedure can be used in all individuals classified by any of various means as alcoholics or alcohol abusers, except those in which the administration of an opiate antagonist is contraindicated and those suffering from Korsakoff's syndrome. (The extinction procedure would probably work poorly in patients with Korsakoff's syndrome.)

The patients can be interviewed to determine the alcoholic beverages they usually drink and the drinking situations in which they normally imbibe. They can then be informed that unlike most treatments, this one does not involve immediately becoming abstinent; instead, their alcohol drinking is to be slowly diminished over many days and only after that will they have to abstain. This procedure should also help to reduce the severity of withdrawal symptoms that are often produced by abrupt termination of alcohol intake.

The patient can then have an opiate antagonist administered shortly before beginning to drink an alcoholic beverage. Examples of opiate antagonists are naloxone, naltrexone, cyclazocine, diprenorphine, etazocine, levalorphan, metazocine, nalorphine, and their salts. The preferred opiate antagonists are naloxone and naltrexone, both of which have been approved for use in humans and have been shown to be free of severe side-effects. Neither is addicting or habit forming. The preferred dose range for naloxone is 0.4 to 10 mg daily if taken by injection; the dose would have to be much larger if it were taken orally. The preferred dose range for naltrexone is 50 to 200 mg daily. The dose administered in a specific case will depend upon the age and weight of the patient, the frequency of administration, and the route of administration, but must be sufficient to assure that the antagonist will be present in sufficient quantities in the body throughout the entire evening of alcohol drinking. The antagonist could be administered in such a way that it is continually present in the body throughout the weeks of extinction therapy. Administration in a way that allows the patient to be free of pharmacologically-active quantities of the antagonist during the following day may be preferred, since it allows the alcoholic to eat food and drink non-alcoholic beverages during the daytime without interference from the antagonist. In the latter case, the patient will be under strict orders to confine all alcohol drinking to the evening hours after the antagonist has been administered.

Examples of routes of administration for the antagonist are injection, oral consumption in any form, transdermal administration, slow-release injection, nasal administration, sublingual administration, implantable drug delivery depots, and the like. A non-obtrusive, non-painful route would be preferred.

The first extinction session (i.e., drinking after administration of the antagonist) can be conducted under close supervision in the treatment center. It is important that later extinction sessions be conducted in the same drinking situations and with the same alcoholic beverages that the patient usually has employed in the past. The stimuli from these specific beverages and situations help to elicit somewhat separate alcohol-drinking responses for the individual. For example, in a particular alcoholic, the alcohol-drinking response of having beers while watching a game on TV may be at least partly independent of his responses of imbibing cocktails at a party or drinking whiskey at a bar. Each should be extinguished in order to assure the generality of the treatment. Although the alcoholic should be encouraged to drink alcohol in the extinction sessions, there should be no social reinforcement for doing so.

The number of extinction sessions required for each patient will depend upon the severity of his or her alcoholism and the number of specific drinking situations in which the alcohol-drinking response must be extinguished. The duration of the extinction program may therefore range from about 1 to 5 weeks.

Once the alcohol-drinking response has been sufficiently weakened, the final extinction sessions could be conducted along with an element of punishment. Examples of punishment include mild electric shock when the alcohol is consumed, production of conditioned taste aversion from very large doses of alcohol with or without emetics, aversion therapy with an alcohol-sensitizing compound such as disulfiram or cyanamide, and the like.

After the final extinction session, the patient is told to abstain from all alcohol in the future. Various procedures can then be used to help ensure that the patient does in fact refrain from drinking alcohol. Such procedures include counselling, psychotherapy, family therapy, job therapy, joining Alcoholics Anonymous and the like. Efforts should also be taken to help the patient resume a normal productive life.

The patient should also be informed that although his or her alcohol-drinking response has been extinguished in the most frequently used drinking situations, it is possible that some have been missed. Consequently, if the patient anticipates or is experiencing a situation in which the response has not been extinguished, he or she should request additional extinction sessions involving this new situation. Alternatively, the patient could be kept on a maintenance program with continued administration of the opiate antagonist.

The present invention is further illustrated by the following example.

EXAMPLE

Extinction of alcohol drinking in 3 strains of rats

Methods

The effects of drinking alcohol after being injected with naloxone was studied in male rats of the AA strain developed for very high levels of alcohol drinking by selective breeding, in male Long Evans rats, and in male Wistar rats. In each case the animals first had several weeks of continual access to 10% (v/v) ethanol, plus food and water, during which time their alcohol drinking increased rapidly at first and eventually, after 3 to 4 weeks, approached a stable asymptotic level. They were then switched to having access to 10% alcohol for only 1 hour each day. After alcohol consumption had stabilized, the rats of each strain were divided into groups matched for alcohol consumption during the last week of 1 hour daily access. One group in each strain was then injected with 10 mg/kg naloxone hydrochloride 5 minutes before their hour of alcohol access for the next 4 days and a control group was injected with a similar volume of saline. There was a third group ("unpaired naloxone") of Wistar rats that was injected with 10 mg/kg of naloxone 3 hours after the end of their hour of alcohol access. The alcohol drinking during 1 hour on the day after the last injection was also recorded. The Long Evans rats were then switched back to continual access to alcohol and their intake measured for the next 13 days.

Results

Figure 2:
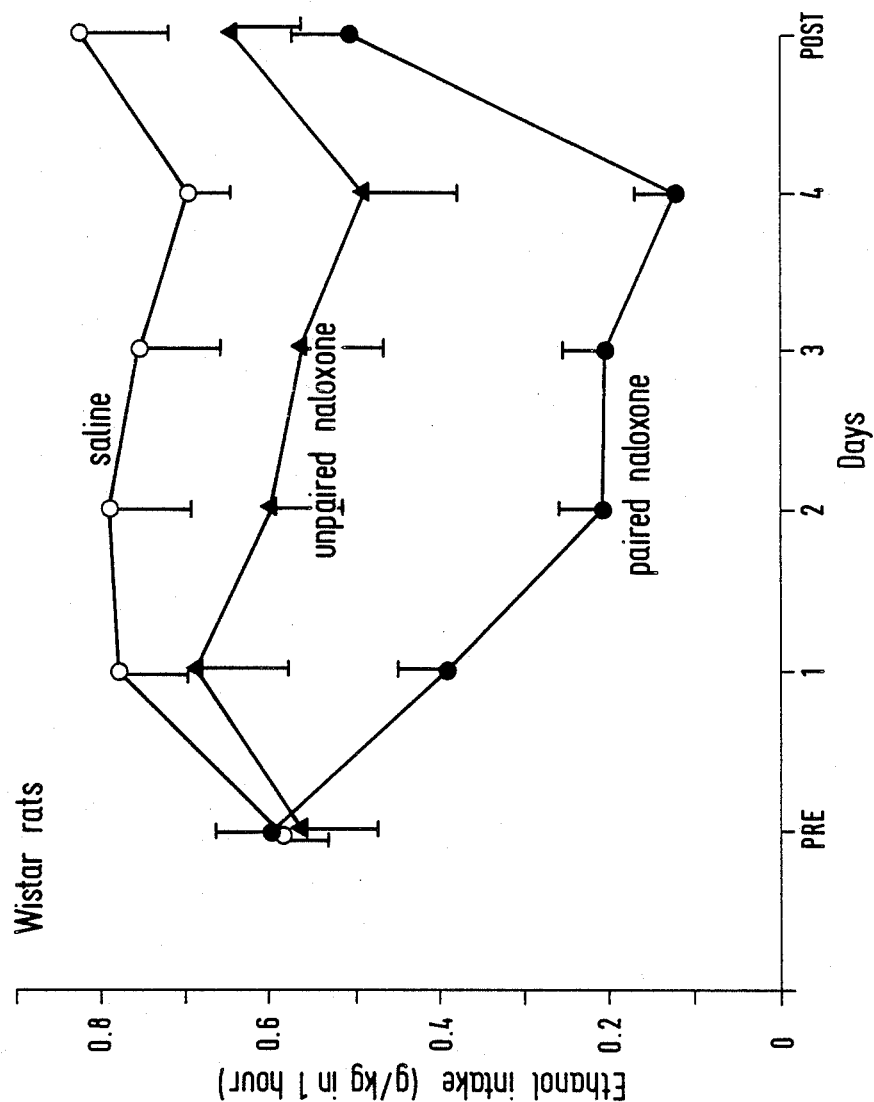
FIG. 2 shows the apparent extinction of alcohol drinking in Wistar rats caused by 4 daily sessions when naloxone was administered 5 minutes before the hour of drinking alcohol ("paired naloxone" group) and the lack of effect of naloxone injected each day 3 hours after alcohol drinking ("unpaired naloxone" group).

Administering naloxone before providing access to alcohol progressively decreased alcohol drinking in all 3 strains (FIGS. 1 and 2). By the fourth day it was almost abolished in each strain, and the alcohol intake was significantly ($p < 0.05$) lower than both the "pre" level (during the preceding week) and the level after the first naloxone injection. The saline controls tended to increase their alcohol intake across days, perhaps due to the stress of injection, and drank significantly more alcohol than the rats given naloxone before alcohol on at least the last 3 extinction days and on the "post" day, 24 hours after the last injection.

Figure 3:
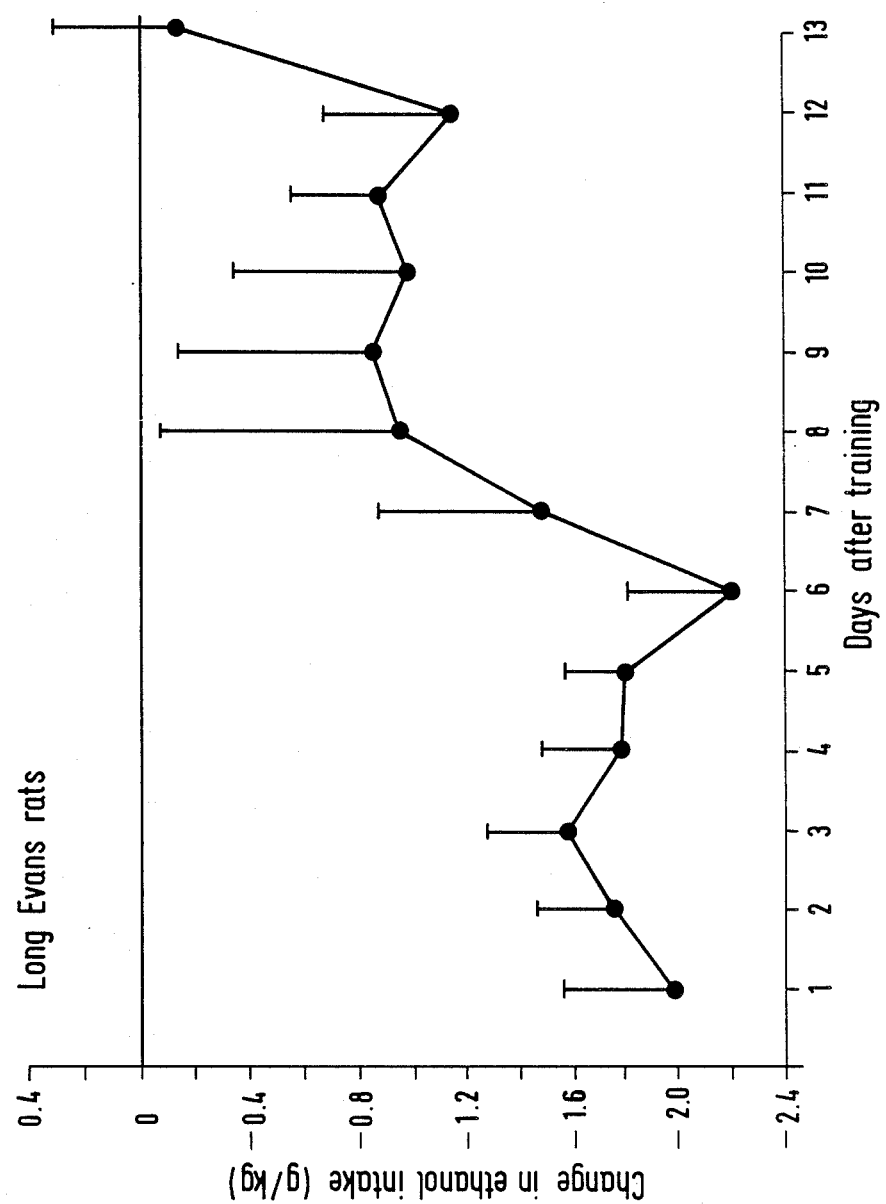
FIG. 3 shows the continued reduction in alcohol drinking by the Long Evans rats that had previously undergone extinction (see FIG. 1) relative to their controls. No naloxone was administered during this time, but the rats treated before with naloxone drank significantly less than the controls on each of the first 7 days. They eventually returned to the control level, apparently because they were not made to abstain completely, did drink some alcohol, and thus relearned the alcohol-drinking response.

The subsequent alcohol drinking by the Long Evans rats is shown in FIG. 3. The rats subjected to extinction with naloxone continued to drink significantly less alcohol than their saline controls on each day of the first week and then gradually returned to the control level. The latter is probably the result of relearning the alcohol-drinking response. Consistent with the common finding that a response is reacquired after extinction more rapidly than it is initially acquired, they took less than 2 weeks to reacquire the response, whereas naive Long Evans rats (i.e., ones that have never had alcohol before) require 3 to 4 weeks to reach this level of alcohol intake.

The Wistar rats given naloxone 3 hours after alcohol drinking ("unpaired naloxone") did not differ significantly from the controls at any time (FIG. 2); their slightly lower intake can probably be attributed to the fact that, unlike the controls, they were not stressed by injection immediately before having access to alcohol. The "unpaired naloxone" group drank significantly more alcohol than the "paired naloxone" group on each of the 4 extinction days. This suggests that the reduction in alcohol drinking was caused specifically by the experience acquired while naloxone was paired with alcohol drinking.

These results are all consistent with the hypothesis that consuming alcohol while naloxone is present causes the alcohol-drinking response to be extinguished. Water intake and body weight were not reduced and there were no indications of any effects detrimental to the health of the animals.

I claim:

1. A method for treating alcoholism by extinguishing the alcohol-drinking response, comprising the steps of:
   repeatedly administering to a subject suffering from alcoholism, an opiate antagonists selected from the group consisting of naloxone, naltrexone, cyclazocine, diprenorphine, etazocine, levalorphan, metazocine, nalorphine and salts thereof in a daily dosage sufficient to block the stimulatory effect of alcohol;
   while the amount of antagonist in the subject's body is sufficient to block the stimulatory effect of alcohol, having the subject drink an alcoholic beverage; and
   continuing the steps of administration of the opiate antagonist and drinking of an alcoholic beverage until the alcohol-drinking response is extinguished.

2. The method of claim 1 further comprising the step of punishing the patient after the alcoholic beverage is consumed, said step of punishment being selected from the group consisting of administration of electric shock, administration of emetics, and administration of an alcohol sensitizing compound.

3. The method of claim 2 wherein the alcohol sensitizing compound is disulfiram or cyanamide.

4. The method of claim 1 further comprising continuing the administration of an opiate antagonist after the alcohol-drinking response is extinguished.

5. The method in accordance with claim 1 wherein the opiate antagonist is naloxone.

6. The method in accordance with claim 5 wherein the dose of naloxone is from 0.2 to 30 mg daily.

7. The method in accordance with claim 1 wherein the opiate antagonist is naltrexone.

8. The method in accordance with claim 7 wherein the dose of naltrexone is from 20 to 300 mg daily.

* * * * *